United States Patent [19]
Woitun et al.

[11] 3,932,642
[45] Jan. 13, 1976

[54] BIOCIDAL COMPOSITIONS CONTAINING A 2-(5'-NITRO-2'-FURYL)-THIENO[2,3-D] PYRIMIDINE AND METHODS OF USE

[75] Inventors: Eberhard Woitun; Wolfgang Reuter, both of Biberach an der Riss, Germany

[73] Assignee: Boehringer Ingelheim GmbH, Ingelheim am Rhein, Germany

[22] Filed: July 19, 1974

[21] Appl. No.: 490,114

Related U.S. Application Data

[62] Division of Ser. No. 241,414, April 5, 1972, Pat. No. 3,830,813.

[30] Foreign Application Priority Data

Apr. 10, 1971 Germany............................ 2117658

[52] U.S. Cl. ............................................. 424/251
[51] Int. Cl.² ......................................... A01N 9/22
[58] Field of Search ................................... 424/251

[56] References Cited
UNITED STATES PATENTS
3,661,908  5/1972  Woitun et al. ............... 260/256.5 R Primary Examiner—Albert T. Meyers
Assistant Examiner—Allen J. Robinson
Attorney, Agent, or Firm—Hammond & Littell

[57] ABSTRACT

Biocidal pharmaceutical compositions containing as an active ingredient a compound of the formula

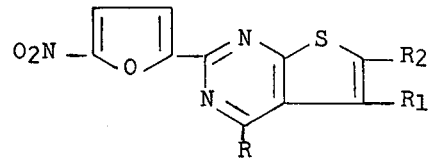

wherein
R is free amino; lower aliphatic acylamino optionally mono- or di-chloro-substituted on the acyl moiety; (straight or branched monoalkyl of 1 to 5 carbon atoms)-amino; di(alkyl of 1 to 4 carbon atoms)amino, where the alkyl moieties may be identical to or different from each other; mono- or di-hydroxy (straight or branched alkyl of 1 to 5 carbon atoms) amino, where the amino nitrogen may have an alkyl of 1 to 4 carbon atoms substituent attached thereto; di-[hydroxy (straight or branched alkyl of 1 to 3 carbon atoms)]amino; alkoxy of 1 to 2 carbon atoms (alkyl of 1 to 3 carbon atoms)amino; free amino (alkyl of 1 to 3 carbon atoms)amino; N-acetyl-(alkylene of 1 to 3 carbon atoms)-diamino; piperidino; or hydroxy-piperidino; and
$R_1$ and $R_2$, which may be identical to or different from each other, are each hydrogen, methyl or ethyl
or a non-toxic, pharmacologically acceptable acid addition salt thereof, and methods of using the same as bactericides, fungicides and trichomonacides.

12 Claims, No Drawings

BIOCIDAL COMPOSITIONS CONTAINING A 2-(5'-NITRO-2'-FURYL)-THIENO(2,3-D) PYRIMIDINE AND METHODS OF USE

This is a division of copending application Ser. No. 241,414, filed Apr. 5, 1972, now U.S. Pat. No. 3,830,813.

This invention relates to novel biocidal pharmaceutical compositions containing a 2-(5'-nitro-2'-furyl)-thieno[2,3-d] pyrimidine or a non-toxic acid addition salt thereof, as well as to methods of using the same as bactericides, fungicides and trichomonacides.

More particularly, the present invention relates to novel biocidal pharmaceutical compositions containing as an active ingredient a 2-(5'-nitro-2'-furyl)-thieno[2,3-d] primidine of the formula

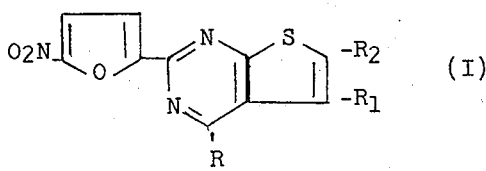

wherein

R is free amino; lower aliphatic acylamino optionally mono- or di-chloro-substituted on the acyl moiety; (straight or branched monoalkyl of 1 to 5 carbon atoms)-amino; di(alkyl of 1 to 4 carbon atoms) amino, where the alkyl moieties may be identical to or different from each other; mono- or di-hydroxy (straight or branched alkyl of 1 to 5 carbon atoms) amino, where the amino nitrogen may have an alkyl of 1 to 4 carbon atoms substituent attached thereto; di-[hydroxy (straight or branched alkyl of 1 to 3 carbon atoms)] amino; alkoxy of 1 to 2 carbon atoms (alkyl of 1 to 3 carbon atoms) amino; free amino (alkyl of 1 to 3 carbon atoms) amino; N-acetyl-(alkylene of 1 to 3 carbon atoms)-diamino; piperidino; or hydroxy-piperidino; and $R_1$ and $R_2$, which may be identical to or different from each other, are each hydrogen, methyl or ethyl; or non-toxic, pharmacologically acceptable acid addition salt thereof.

The compounds embraced by formula I may be prepared by the following methods:

METHOD A

For the preparation of a compound of the formula I wherein R has the meanings defined in formula I except mono- or di-chloro-substituted lower aliphatic acylamino, by reacting a 2-(5'-nitro-2'-furyl)-thieno[2,3-d]pyrimidine of the formula

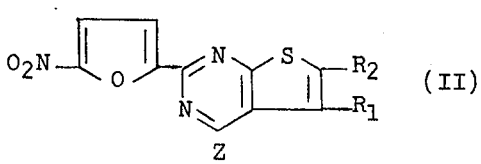

wherein $R_1$ and $R_2$ have the same meanings as in formula I, and

Z is halogen or free or substituted mercapto, with an amine of the formula $$R' - H \qquad (III)$$

wherein R' has the same meanings as R in formula I except mono-or di-chloro-substituted lower aliphatic acylamino.

The reaction is preferably performed in an inert organic solvent or suspension medium at a temperature between 20° and 150°C., and in those instances where Z in formula II is halogen the presence of a hydrogen halide-binding agent is required.

The hydrogen halide-binding agent may be an equimolar amount of an inorganic or tertiary organic base or a molar excess of the amine of the formula III.

The reaction is most advantageously performed in a polar organic solvent medium, such as an alkanol, dimethylformamide, dimethylsulfoxide, 1-methyl-2-pyrrolidinone or hexamethylphosphoric acid triamide.

If it is desired to prepare by this method a compound of the formula I wherein R is free amino(alkyl of 1 to 3 carbon atoms)amino, it is more advantageous to react a compound of the formula II with an amine of the formula III in which R' is N-acyl-(alkylene of 1 to 3 carbon atoms)-diamine and subsequently split off the N-acyl substituent of the reaction product by acid hydrolysis.

METHOD B

By reacting a 2-(2'-furyl)-thieno[2,3-d]pyrimidine of the formula

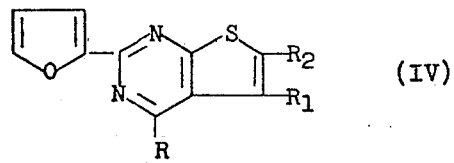

wherein R, $R_1$ and $R_2$ have the same meanings as in formula I, with a nitrating agent, such as nitric acid, a mixture of nitric acid and sulfuric acid, or a mixture of nitric acid and acetanhydride.

In those instances where the substituent R of the starting compound of the formula IV comprises one or more free hydroxyl or amino groups, these groups are provided by conventional methods with suitable protective substituents, such as acyl, prior to the reaction with the nitrating agent. After completion of the nitration reaction the protective substituents may be split off again by conventional methods, such as by acid hydrolysis.

The nitration reaction generally requires reaction temperatures of 0° to 30°C, and in some instances it is advantageously performed in an inert solvent or diluent.

METHOD C

By reacting a 2-(5'-bromo-2'-furyl)-thieno[2,3-d]pyrimidine of the formula

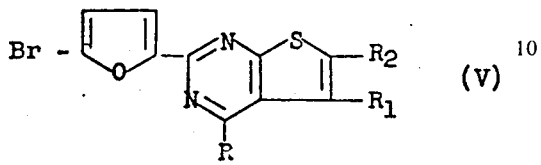

(V)

wherein R, $R_1$ and $R_2$ have the same meanings as in formula I, with a salt of nitrous acid in the presence of a polar solvent and at a temperature between 0° and 120°C.

Examples of preferred salts of nitrous acid are alkali metal or alkaline earth metal nitrites.

Examples of suitable polar solvents are aliphatic organic acids, such as glacial acetic acid, dimethylformamide or dimethylsulfoxide.

METHOD D

By reacting a 2-(5'-carboxy-2'-furyl)-thieno[2,3-d]pyrimidine of the formula

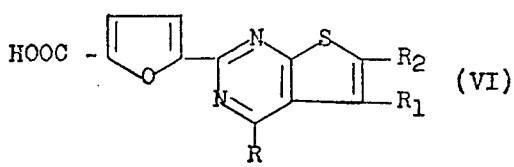

(VI)

wherein R, $R_1$ and $R_2$ have the same meanings as in formula I, with nitric acid or a salt of nitric acid in the presence of a strong mineral acid, such as concentrated sulfuric acid, at a temperature between −20° and +50°C., preferably from 0° to +20°C.

The mineral acid is advantageously provided in an amount such that it simultaneously serves as the solvent medium for the reaction.

Examples of suitable salts of nitric acid are alkali metal or alkaline earth metal nitrates.

In those instances where substituent R in formula VI comprises free amino or hydroxyl groups, these are provided in conventional manner with protective substituents, such as acyl, prior to the nitration reaction; after completion of the reaction the protective groups may, if desired, by split off again by conventional methods, such as by acid hydrolysis.

METHOD E

For the preparation of a compound of the formula I wherein R is acylamino or mono- or di-chloro-substituted acylamino, by acylating a 2-(5'-nitro-2'-furyl)-4-aminothieno[2,3-d]pyrimidine of the formula

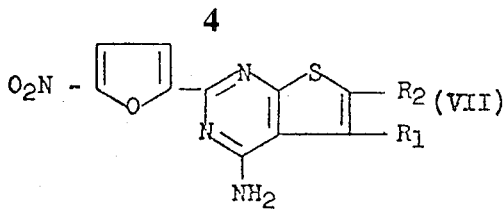

(VII)

wherein $R_1$ and $R_2$ have the same meanings as in formula I, with a conventional acylating agent, such as an acid halide or an acid anhydride, at a temperature up to the boiling point of the particular acylating agent which is employed.

The starting compounds required for methods A to E are either known compounds or may be prepared by known methods.

Thus, the starting compounds of the formula II wherein Z is halogen may be prepared by reacting a 5-nitrofuran-2-iminocarboxylic acid ester [see W. R. Sherman et al, J. Med. Chem. 8, 25 (1965)] with a 2-aminothiophene-3-carboxylic acid ester [see K. Gewald, Chem. Ber. 98, 3571 (1965); and ibid, 99, 94 (1966)], followed by halogenation of the intermediately formed 2-(5'-nitro-2'-furyl)-4-hydroxy-thieno[2,3-d]pyrimidine with a conventional halogenating agent, such as a phosphorus oxyhalide, phosphorus pentahalide or thionyl halide.

The compounds of the formula II wherein Z is free or substituted mercapto may, for example, be prepared by reacting a corresponding 4-halo-substituted thieno[2,3-d]pyrimidine with thiourea, followed by optional alkylation of resulting 4-mercapto compound with an alkyl halide.

The starting compounds of the formula IV may be prepared by reacting a furan-2-imino-carboxylic acid ester [see A. Pinner, Chem. Ber. 25, 1416 (1892)] with a 2-aminothiophene-3-carboxylic acid ester to form the corresponding 2-(2'-furyl)-4-hydroxy-thieno[2,3-d]pyrimidine, halogenating the latter with a conventional halogenating agent, such as a phosphorus oxyhalide, and reacting the intermediately formed corresponding 2-(2'-furyl)-4-halo-thieno[2,3-d]pyrimidine with an amine of the formula R — H, where R has the meanings defined in connection with formula I.

The starting compounds of the formula V may, for instance, be obtained by treating a corresponding 2-(2'-furyl)-4-halo-thieno[2,3-d]pyrimidine with a stoichiometric amount of bromine, and reacting the resulting 2-(5'-bromo-2'-furyl)-4-halo-thieno[2,3-d]pyrimidine with an amine of the formula R — H, where R has the same meanings as in formula I. The bromination reaction is preferably performed in an organic solvent medium and in the presence of a hydrogen halide-binding agent at a temperature between 0° and 30°C. Suitable organic solvent media are inert solvents, such as 1,2-dichloroethane, as well as polar solvents, such as glacial acetic acid. An example of a suitable hydrogen halide-binding agent is anhydrous sodium acetate. The subsequent reaction with the amine R — H is performed at elevated temperatures, and the amine is preferably provided in sufficient excess over the stoichiometrically required amount to serve simultaneously as the hydrogen halide-binding agent and the solvent medium for the reaction.

The starting compounds of the formula VI may be prepared by reacting a 5-carbalkoxy-furan-2-iminocarboxylic acid ester with a 2-amino-thiophene-3-carboxylic acid ester, halogenating the intermediate thus obtained with a halogenating agent, such as a phosphorus oxyhalide, reacting the halogenation product with an amine of the formula R — H, where R has the same meanings as in formula I, and hydrolizing the reaction product in the presence of an acid, such as hydrochloric acid.

Finally, the starting compounds of the formula VII are obtained by reacting a compound of the formula II with ammonia.

The end products of the formula I obtained by methods A through E are organic bases and therefore form acid addition salts with inorganic or organic acids. Examples of non-toxic, pharmacologically acceptable acid addition salts are those formed with hydrochloric acid, hydrobromic acid, sulfuric acid, tartaric acid, adipic acid, maleic acid, citric acid, 8-chlorotheophylline or the like.

The following examples further illustrate the present invention and will enable others skilled in the art to understand it more completely. It should be understood, however, that the invention is not limited solely to the particular examples given below:

PREPARATION OF STARTING COMPOUNDS

EXAMPLE A 2-(5'-Nitro-2'-furyl)-4-hydroxy-thieno[2,3-d]pyrimidine

A mixture consisting of 18.4 gm (0.1 mol) of 5-nitrofuran-2-iminocarboxylic acid methyl ester, 15.7 gm (0.1 mol) of 2-amino-thiophene-3-carboxylic acid methyl ester and 50 ml of xylene was heated to reflux temperature. After about two hours crystals began to separate out of the clear solution, and after a reaction period of 20 hours the reaction mixture was cooled, the precipitate formed thereby was collected by vacuum filtration, and the filter cake was washed with ether and recrystallized from dimethylformamide, yielding 10.4 gm (40% of theory) of 2-(5'-nitro-2'-furyl)-4-hydroxy-thieno[2,3-d]pyrimidine, m. p. >300°C.

Analysis: $C_{10}H_5N_3O_4S$; mol. wt. 263.24: Calculated (percent): C, 45.62; H, 1.92; N, 15.97. Found (percent): C, 45.68; H, 1.97; N, 15.88.

In analogous manner the following compounds were prepared:

a. 5-Methyl-2-(5'-nitro-2'-furyl)-4-hydroxy-thieno[2,3-d]pyrimidine, m. p. >300°C. (from dimethylformamide), from 5-nitro-furan-2-iminocarboxylic acid ether ester and 2-amino-4-methyl-thiophene-3-carboxylic acid methyl ester.

b. 6-Methyl-2-(5'-nitro-2'-furyl)-4-hydroxy-thieno[2,3-d]pyrimidine, m. p. >300°C. (from dimethylformamide), from 2-amino-5-methyl-thiophene-3-carboxylic acid methyl ester and 5-nitro-furan-2-iminocarboxylic acid ethyl ester.

c. 6-Ethyl-2-(5'-nitro-2'-furyl)-4-hydroxy-thieno[2,3-d]pyrimidine, m. p. 271°–273°C. (decomp.; from dimethylformamide), from 5-nitro-furan-2-iminocarboxylic acid ethyl ester and 5-ethyl-2-aminothiophene-3-carboxylic acid methyl ester.

d. 5,6-Dimethyl-2-(5'-nitro-2'-furyl)-4-hydroxy-thieno[2,3-d]pyrimidine, m. p. >300°C. (from dimethylformamide), from 5-nitro-furan-2-iminocarboxylic acid ethyl ester and 2-amino-4,5-dimethyl-thiophene-3-carboxylic acid methyl ester.

EXAMPLE B

4-Chloro-2-(5'-nitro-2'-furyl)-thieno[2,3-d]pyrimidine

A mixture consisting of 26.3 gm (0.1 mol) of 2-(5'-nitro-2'-furyl)-4-hydroxy-thieno[2,3-d]pyrimidine and 150 ml of phosphorus oxychloride was refluxed for two hours while stirring. Thereafter, the excess, unreacted phosphorus oxychloride was distilled off in vacuo, and the residue was decomposed with water. The crystalline substance formed thereby was collected by vacuum filtration, dried and recrystallized from dimethylformamide, yielding 26.5 gm (94% of theory) of 4-chloro-2-(5'-nitro-2'-furyl)-thieno[2,3-d]pyrimidine, m. p. 245°–247°C.

Analysis: $C_{10}H_4Cl\,N_3O_3S$; mol. wt. 281.69: Calculated (percent): C, 42.64; H, 5.01; Cl, 12.49. Found (percent): C, 42.76; H, 5.10; Cl, 12.42.

In analogous manner, the following 4-chloro-2-(5'-nitro-2'-furyl)-thieno[2,3-d]pyrimidines of the formula II were prepared:

a. 4-Chloro-5-methyl-2-(5'-nitro-2'-furyl)-thieno[2,3-d]pyrimidine, m. p. 220°–222°C. (from dioxane), from 5-methyl-2-(5'-nitro-2'-furyl)-4-hydroxy-thieno[2,3-d]pyrimidine and phosphorus oxychloride.

b. 4-Chloro-6-methyl-2-(5'-nitro-2'-furyl)-thieno[2,3-d]pyrimidine, m. p. 194°–196°C. (from ethanol), from 6-methyl-2-(5'-nitro-2'-furyl)-4-hydroxy-thieno[2,3-d]pyrimidine and phosphorus oxychloride.

c. 6-Ethyl-4-chloro-2-(5'-nitro-2'-furyl)-thieno[2,3-d]pyrimidine, m. p. 108°–109°C. (from ethanol), from 6-ethyl-2-(5'-nitro-2'-furyl)-4-hydroxy-thieno[2,3-d]pyrimidine and phosphorus oxychloride.

d. 4-Chloro-5,6-dimethyl-2-(5'-nitro-2'-furyl)-thieno[2,3-d]pyrimidine m. p. 230°–232°C. (from dioxane), from 5,6-dimethyl-2-(5'-nitro-2'-furyl)-4-hydroxy-thieno[2,3-d]pyrimidine and phosphorus oxychloride.

EXAMPLE C

4-Mercapto-2-(5'-nitro-2'-furyl)-thieno[2,3-d]pyrimidine

A refluxing solution of 2.8 gm (0.01 mol) of 4-chloro-2-(5'-nitro-2'-furyl)-thieno[2,3-d]pyrimidine in 50 ml of dimethylformamide was admixed with 9.5 gm (0.125 mol) of thiourea, and the mixture was allowed to reflux for one minute more. Thereafter, the reaction solution was cooled to room temperature, allowed to stand at room temperature for five minutes, and was then poured into 1 liter of ice water. The crystalline precipitate formed thereby was collected by vacuum filtration, dried and recrystallized from methyl ethyl ketone/ethyl acetate, yielding 1.4 gm (50% of theory) of 4-mercapto-2-(5'-nitro-2'-furyl)-thieno[2,3-d]pyrimidine, m. p. 192°–193°C. (decomp.).

Analysis: $C_{10}H_5N_3O_3S_2$; mol. wt. 279.30: Calculated (percent): C, 43.00; H, 1.81; N, 15.05. Found (percent): C, 43.20; H, 1.85; N, 15.30.

EXAMPLE D

4-Methylmercapto-2-(5'-nitro-2'-furyl)-thieno[2,3-d]pyrimidine

A solution of 1.4 gm (0.005 mol) of the end product of Example C in 50 ml of dimethylsulfoxide was admixed at room temperature, and while stirring, first with 0.85 gm (0.006 mol) of methyl iodide and then gradually with 0.42 gm (0.006 mol) of potassium methylate, and the resulting mixture was stirred at room temperature for 30 minutes more. Thereafter, the reaction mixture was poured into 0.75 liter of ice water, and the crystalline precipitate formed thereby was collected by vacuum filtration and recrystallized from dimethylformamide, yielding 0.8 gm (55% of theory) of 4-methylmercapto-2-(5'-nitro-2'-furyl)-thieno[2,3-d]pyrimidine, m. p. 264°–265°C.

Analysis: $C_{11}H_7N_3O_3S_2$; mol. wt. 293.33: Calculated (percent): C, 45.05; H, 2.41; N, 14.33. Found (percent): C, 45.00; H, 2.45; N, 14.45.

EXAMPLE E 2-(2'-Furyl)-4-hydroxy-thieno[2,3-d]pyrimidine 36.8 gm (0.2 mol) of ethyl furan-2-iminocarboxylate and 33.0 gm (0.21 mol) of methyl 2-amino-thiophene-3-carboxylate were dissolved in 150 ml of xylene, and the solution was heated at 140°C. for 50 hours. Thereafter, the reaction solution was allowed to cool, and the crystalline precipitate formed thereby was collected by vacuum filtration and recrystallized from dioxane in the presence of activated charcoal. 18.2 gm (42% of theory) of 2-(2'-furyl)-4-hydroxy-thieno[2,3-d]pyrimidine, m. p. 242°–243°C., were obtained.

Analysis: $C_{10}H_6N_2O_2S$; mol. wt. 218.24: Calculated (percent): C, 55.00; H, 2.77; N, 12.84. Found (percent): C, 55.10; H, 2.81; N, 12.64.

EXAMPLE F

4-Chloro-2-(2'-furyl)-thieno[2,3-d]pyrimidine

A mixture consisting of 21.8 gm (0.1 mol) of 2-(2'-furyl)-4-hydroxy-thieno[2,3-d]pyrimidine and 75 ml of phosphorus oxychloride was refluxed for one hour, whereby everything went into solution. Thereafter, the excess, unreacted phosphorus oxychloride was distilled off in vacuo, and the residue was poured into ice water. The crystalline precipitate formed thereby was collected by vacuum filtration, washed with water and recrystallized from ethanol, yielding 17.1 gm (72% of theory) of 4-chloro-2-(2'-furyl)-thieno[2,3-d]pyrimidine, m. p. 133°134°C.

Analysis: $C_{10}H_5Cl\ N_2O\ S$; mol. wt. 236.70: Calculated (percent): C, 50.75; H, 2.13; N, 11.82. Found (percent): C, 50.63; H, 2.19; N, 11.71.

EXAMPLE G

4-Dibutylamino-2-(2'-furyl)-thieno[2,3-d]pyrimidine

A solution of 4.7 gm (0.02 mol) of 4-chloro-2-(2'-furyl)-thieno[2,3-d]pyrimidine and 20 ml of dibutylamine in 75 ml of ethanol was refluxed for 15 minutes and then poured into water. The aqueous mixture was extracted with methylene chloride, the organic extract was washed with water, dried over sodium sulfate and evaporated in vacuo, and the residue was recrystallized from petroleum ether, yielding 4.3 gm (65% of theory) of 4-dibutylamino-2-(2'-furyl)-thieno[2,3-d]pyrimidine, m. p. 69°–70°C.

Analysis: $C_{16}H_{23}N_3O\ S$; mol. wt. 329.47: Calculated (percent): C, 65.61; H, 7.04; N, 12.75. Found (percent): C, 65.70; H, 7.11; N, 12.73.

EXAMPLE H 2-(5'-Bromo-2'-furyl)-4-chloro-thieno[2,3-d]pyrimidine

A small amount of hydroquinone and sulfur were added to a solution of 2.4 gm (0.01 mol) of 4-chloro-2-(2'-furyl)-thieno[2,3-d]pyrimidine in 100 ml of dichloroethane, and then a solution of 8.0 gm (0.01 mol) of bromine in 20 ml of dichloroethane was added dropwise over a period of 30 minutes to the mixture at room temperature, and the resulting mixture was allowed to stand for two hours at room temperature. Thereafter, the reaction mixture was poured into water, the organic phase was separated, and the aqueous phase was extracted once with dichloroethane. The extract solution was combined with the organic phase, the mixed solution was washed once with an aqueous sodium thiosulfate solution and once with water, evaporated in vacuo, and the residue was recrystallized from ethyl acetate, yielding 1.9 gm (60% of theory) of 2-(5'-bromo-2'-furyl)-4-chloro-thieno[2,3-d]pyrimidine, m. p. 194°–195 C.

Analysis: $C_{10}H_4BrClN_2O\ S$; mol. wt. 313.60: Calculated (percent): C, 38.30; H, 1.29; N, 8.93. Found (percent): C, 38.44; H, 1.41; N, 8.72.

EXAMPLE I 2-(5'-Bromo-2'-furyl)-4-($\beta$-hydroxyethyl-amino)-thieno[2,3-d]pyrimidine A mixture consisting of 1.6 gm (0.005 mol) of 2-(5'-bromo-2'-furyl)-4-chloro-thieno[2,3-d]pyrimidine, 5 ml of 2-amino-ethanol-1 and 20 ml of ethanol was heated at 60°C. for 15 minutes. Thereafter, the resulting solution was poured over ice, and the precipitate formed thereby was collected by vacuum filtration, washed with water and recrystallized from methyl ethyl ketone, yielding 1.2 gm (72% of theory) of 2-(5'-bromo-2'-furyl)-4-($\beta$-hydroxyethyl-amino)-thieno[2,3-d]pyrimidine, m. p. 219°–220°C.

Analysis: $C_{12}H_{10}BrN_3O_2S$; mol. wt. 340.22: Calculated (percent): C, 42.37; H, 2.96; N, 12.35. Found (percent): C, 42.50; H, 3.06; N, 12.40.

EXAMPLE J 2-(5'-Carbomethoxy-2'-furyl)-4-hydroxy-thieno[2,3-d]pyrimidine 1.8 gm (0.01 mol) of methyl 5-carbomethoxy-furan-2-iminocarboxylate (m. p. 82°–83°C.; prepared from 5-carbomethoxy-furan-2-carbonitrile, methanol and hydrochloric acid) and 1.7 gm (0.11 mol) of methyl 2-amino-thiophene-3-carboxylate were intimately admixed with each other, and the mixture was heated at 140°C. for 4 hours in a round-bottom flask. After some time a crystalline substance began to separate out of the clear molten mass, and at the end of the heating time the contents of the flask had completely solidified. The solid product was triturated with ethanol, and the insoluble matter was collected by vacuum filtration and recrystallized from dimethylformamide, yielding 1.4 gm (51% of theory) of 2-(5'-carbomethoxy-2'-furyl)-4-hydroxy-thieno[2,3-d]pyrimidine, m. p. 243°–245°C.

Analysis: $C_{12}H_8N_2O_4S$; mol. wt. 276.28: Calculated (percent): C, 48.90; H, 2.38; N, 1.29. Found (percent): C, 48.79; H, 2.47; N, 16.38.

EXAMPLE K 2-(5'-Carbomethoxy-2'-furyl)-4-chloro-thieno[2,3-d]pyrimidine

A mixture consisting of 2.8 gm (0.01 mol) of 2-(5'-carbomethoxy-2'-furyl)-4-hydroxy-thieno[2,3-d]pyrimidine and 20 ml of phosphorus oxychloride was refluxed for 90 minutes, whereby a solution was formed. Thereafter, the excess, unreacted phosphorus oxychloride was distilled off in vacuo, and the residue was poured into ice water. The crystalline precipitate formed thereby was collected by vacuum filtration, dried and recrystallized from a mixture of dimethylformamide and ethanol, yielding 2.6 gm (89% of theory) of 2-(5'-carbomethoxy-2'-furyl)-4-chloro-thieno[2,3-d]pyrimidine, m. p. 185°–187°C.

Analysis: $C_{12}H_7ClN_2O_3S$; mol. wt. 294.73: Calculated (percent): C, 48.90; H, 2.38; Cl, 12.03. Found (percent): C, 48.71; H, 2.45; Cl, 12.19.

EXAMPLE L 2-(5'-Carboxy-2'-furyl)-4-dimethylamino-thieno[2,3-d]pyrimidine

A mixture consisting of 1.45 gm (0.005 mol) of 2-(5'-carboxymethyl-2'-furyl)-4-chloro-thieno[2,3-d]pyrimidine and 10 ml of dimethylamine was heated at 80°C. for one hour in a closed pressure vessel. Thereafter, the excess, unreacted dimethylamine was purged from the vessel, the residual 4-dimethylamino-2-(5'-carboxydimethylamido-2'-furyl)-thieno[2,3-d]pyrimidine was admixed with 10 ml of concentrated hydrochloric acid, and the mixture was refluxed for two hours. Thereafter, the reaction mixture was cooled and then admixed with an equal volume of water, and the precipitate formed thereby was collected by vacuum filtration, washed with a small amount of water and recrystallized from methanol, yielding 0.7 gm (48% of theory) of 2-(5'-carboxy-2'-furyl)-4-dimethylamino-thieno[2,3-d]pyrimidine, m. p. 222°–224°C. (decomp.).

Analysis: $C_{13}H_{11}N_3O_3S$; mol. wt. 289.32. Calculated (percent): C, 53.97; H, 3.83; N, 14.52. Found (percent): C, 54.12; H, 3.91; N, 14.44.

Preparation of end products of the formula I

EXAMPLE 1

4-(β-Hydroxyethyl-amino)-2-(5'-nitro-2'-furyl)-thieno[2,3-d]pyrimidine by method A A solution of 0.61 gm (0.01 mol) of 2-aminoethanol-1 in 5 ml of dimethylsulfoxide was added dropwise to a suspension of 1.4 gm (0.005 mol) of 4-chloro-2-(5'-nitro-2'-furyl)-thieno[2,3-d]pyrimidine in 20 ml of dimethylsulfoxide at 80°C., accompanied by stirring, and the resulting mixture was allowed to stand at that temperature for 30 minutes, whereby a solution was formed. Thereafter, the solution was cooled and then poured into water, and the precipitate formed thereby was collected by vacuum filtration, washed with water and recrystallized from a mixture of ethyl acetate and petroleum ether, yielding 1.2 gm (78% of theory) of the compound of formula

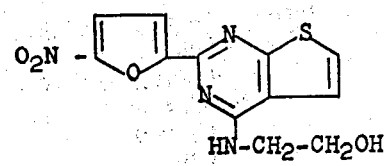

having a melting point of 205°–206°C.

Analysis: $C_{12}H_{10}N_4O_4S$; mol. wt. 306.31: Calculated (percent): C, 47.05; H, 3.29; N, 18.29. Found (percent): C, 47.20; H, 3.35; N, 18.17.

EXAMPLE 2

Using a procedure analogous to that described in Example 1, 4-amino-2-(5'-nitro-2'-furyl)-thieno[2,3-d]pyrimidine, m. p. >300°C. (recrystallized from dimethylformamide), of the formula

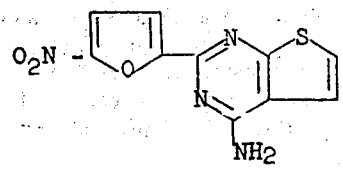

was prepared from 4-chloro-2-(5'-nitro-2'-furyl)-thieno[2,3-d]pyrimidine and ammonia.

EXAMPLE 3

Using a procedure analogous to that described in Example 1, 4-methylamino-2-(5'-nitro-2'-furyl)-thieno[2,3-d]pyrimidine, m. p. 263°–264°C. (recrystallized from dioxane/ethanol), of the formula

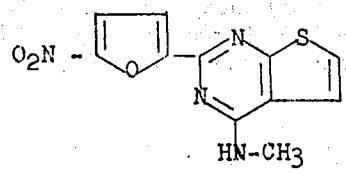

was prepared from 4-chloro-2-(5'-nitro-2'-furyl)-thieno[2,3-d]pyrimidine and methylamine.

EXAMPLE 4

Using a procedure analogous to that described in Example 1, 4-ethylamino-2-(5'-nitro-2'-furyl)-thieno[2,3-d]pyrimidine, m. p. 223°C. (recrystallized from ethanol), was prepared from 4-chloro-2-(5'-nitro-2'-furyl)-thieno[2,3-d]pyrimidine and ethylamine.

EXAMPLE 5

Using a procedure analogous to that described in Example 1, 4-isopropylamino-2-(5'-nitro-2'-furyl)-thieno[2,3-d]pyrimidine, m. p. 196°–198°C. (recrystallized from ethanol), was prepared from 4-chloro-2-(5'-nitro-2'-furyl)-thieno[2,3-d]pyrimidine and isopropylamine.

EXAMPLE 6

Using a procedure analogous to that described in Example 1, 4-n-pentylamino-2-(5'-nitro-2'-furyl)-thieno[2,3-d]pyrimidine, m. p. 130°C. (recrystallized from ethanol), was prepared from 4-chloro-2-(5'-nitro-2'-furyl)-thieno[2,3-d]pyrimidine and n-pentylamine.

EXAMPLE 7

Using a procedure analogous to that described in Example 1, 4-dimethylamino-2-(5'-nitro-2'-furyl)-thieno[2,3-d]pyrimidine, m. p. 226°–229°C. (recrystallized from ethanol/dioxane), of the formula

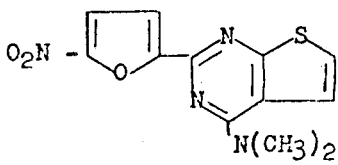

was prepared from 4-chloro-2-(5'-nitro-2'-furyl)-thieno[2,3-d]pyrimidine and dimethylamine.

EXAMPLE 8

Using a procedure analogous to that described in Example 1, 4-(di-n-butylamino)-2-(5'-nitro-2'-furyl)-thieno[2,3-d]pyrimidine, m. p. 102°–103°C. (recrystallized from ethanol), was prepared from 4-chloro-2-(5'-nitro-2'-furyl)-thieno[2,3-d]pyrimidine and di-n-butylamine.

EXAMPLE 9

Using a procedure analogous to that described in Example 1, 4-(ω-hydroxypentyl-amino)-2-(5'-nitro-2'-furyl)-thieno[2,3-d]pyrimidine, m. p. 154°–155°C. (recrystallized from ethanol), was prepared from 4-chloro-2-(5'-nitro-2'-furyl)-thieno[2,3-d]pyrimidine and 5-amino-pentanol-1.

EXAMPLE 10

Using a procedure analogous to that described in Example 1, 4-(β-hydroxypropyl-amino)-2-(5'-nitro-2'-furyl)-thieno[2,3-d]pyrimidine, m. p. 177°–178°C. (recrystallized from ethanol), of the formula

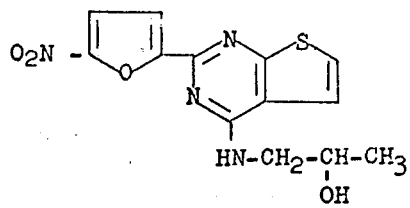

was prepared from 4-chloro-2-(5'-nitro-2'-furyl)-thieno[2,3-d]pyrimidine and 1-amino-propanol-2.

EXAMPLE 11

Using a procedure analogous to that described in Example 1, 4-[(β-hydroxy-α-methyl-ethyl)-amino]-2-(5'-nitro-2'-furyl)-thieno[2,3-d]pyrimidine, m. p. 244°–245°C. (recrystallized from ethanol), of the formula

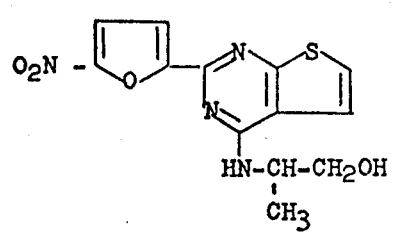

was prepared from 4-chloro-2-(5'-nitro-2'-furyl)-thieno[2,3-d]pyrimidine and 2-hydroxy-1-methyl-ethylamine.

EXAMPLE 12

Using a procedure analogous to that described in Example 1, 4-(β,γ-dihydroxypropyl-amino)-2-(5'-nitro-2'-furyl)-thieno[2,3-d]pyrimidine, m. p. 222°–223°C. (recrystallized from ethanol), of the formula

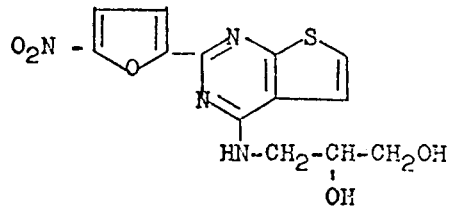

was prepared from 4-chloro-2-(5'-nitro-2'-furyl)-thieno[2,3-d]pyrimidine and 1-amino-2,3-propanediol.

EXAMPLE 13

Using a procedure analogous to that described in Example 1, 4-(β-methoxyethyl-amino)-2-(5'-nitro-2'-furyl)-thieno[2,3-d]pyrimidine, m. p. 170°–171°C. (recrystallized from ethanol), of the formula

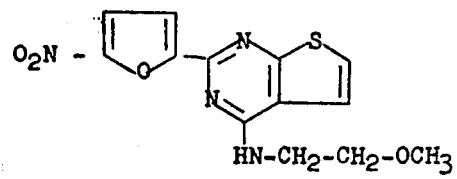

was prepared from 4-chloro-2-(5'-nitro-2'-furyl)-thieno[2,3-d]pyrimidine and β-methoxyethyl-amine.

EXAMPLE 14

Using a procedure analogous to that described in Example 1, 4-(β-ethoxyethyl-amino)-2-(5'-nitro-2'-furyl)-thieno[2,3-d]pyrimidine, m. p. 131°–133°C. (recrystallized from ethanol), was prepared from 4-chloro-2-(5'-nitro-2'-furyl)-thieno[2,3-d]pyrimidine and β-ethoxyethyl-amine.

EXAMPLE 15

Using a procedure analogous to that described in Example 1, 4-(γ-methoxypropyl-amino)-2-(5'-nitro-2'-furyl)-thieno[2,3-d]pyrimidine, m. p. 151°–152°C. (recrystallized from ethanol), was prepared from 4-chloro-2-(5'-nitro-2'-furyl)-thieno[2,3-d]pyrimidine and 3-methoxypropyl-amine.

EXAMPLE 16

Using a procedure analogous to that described in Example 1, 4-[N-(β-hydroxyethyl)-methylamino]-2-(5'-nitro-2'-furyl)-thieno[2,3-d]pyrimidine, m. p. 161°–162°C. (recrystallized from ethanol), of the formula

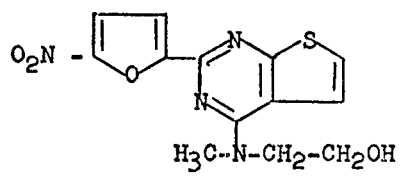

was prepared from 4-chloro-2-(5′-nitro-2′-furyl)-thieno[2,3-d]pyrimidine and 2-methylamino-ethanol.

EXAMPLE 17

Using a procedure analogous to that described in Example 1, 4-[N(β-hydroxyethyl)-n-butylamino]-2-(5′-nitro-2′-furyl)-thieno[2,3-d]pyrimidine, m. p. 132°–133°C. (recrystallized from ethanol), was prepared from 4-chloro-2-(5′-nitro-2′-furyl)-thieno[2,3-d]pyrimidine and 2-(n-butylamino)-ethanol.

EXAMPLE 18

Using a procedure analogous to that described in Example 1, 4-[N-(γ-hydroxypropyl)-methylamino]-2-(5′-nitro-2′-furyl)-thieno[2,3-d]pyrimidine, m. p. 113°–115°C. (recrystallized from ethanol), was prepared from 4-chloro-2-(5′-nitro-2′-furyl)-thieno[2,3-d]pyrimidine and 3-methylamino-propanol.

EXAMPLE 19 using a procedure analogous to that described in Example 1, 4-[N,N-bis-(62-hydroxyethyl)-amino]-2-(5′-nitro-2′-furyl)-thieno[2,3-d]pyrimidine, m. p. 198°–199°C. (recrystallized from ethanol), of the formula

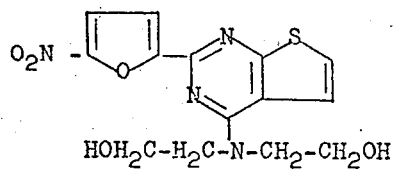

was prepared from 4-chloro-2-(5′-nitro-2′-furyl)-thieno[2,3-d]pyrimidine and bis-(β-hydroxyethyl)-amine.

EXAMPLE 20

Using a procedure analogous to that described in Example 1, 4-[N,N-bis-(β-hydroxypropyl)-amino]-2-(5′-nitro-2′-furyl)-thieno[2,3-d]pyrimidine, m. p. 215°–218°C. (recrystallized from ethanol), was prepared from 4-chloro-2-(5′-nitro-2′-furyl)-thieno[2,3-d]pyrimidine and bis-(β-hydroxypropyl)-amine.

EXAMPLE 21

Using a procedure analogous to that described in Example 1, 4-(3″-hydroxy-piperidino)-2-(5′-nitro-2′-furyl)-thieno[2,3-d]pyrimidine, m. p. 178–179°C. (recrystallized from ethanol), of the formula

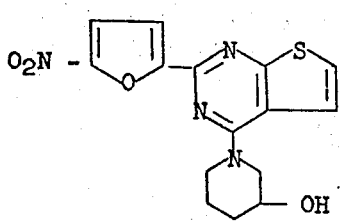

was prepared from 4-chloro-2-(5′-nitro-2′-furyl)-thieno [2,3-d]pyrimidine and 3-hydroxy-piperidine.

EXAMPLE 22

Using a procedure analogous to that described in Example 1, 4-(4″-hydroxy-piperidino)-2-(5′-nitro-2′-furyl)-thieno[2,3-d]pyrimidine, m. p. 230–232°C. (recrystallized from ethanol), was prepared from 4-chloro-2-(5′-nitro-2′-furyl)-thieno[2,3-d]pyrimidine and 4-hydroxy-piperidine.

EXAMPLE 23

Using a procedure analogous to that described in Example 1, 4-(methylamino)-5-methyl-2-(5′-nitro-2′-furyl)-thieno[2,3-d]pyrimidine, m. p. 192°–193°C. (recrystallized from methyl ethyl ketone), of the formula

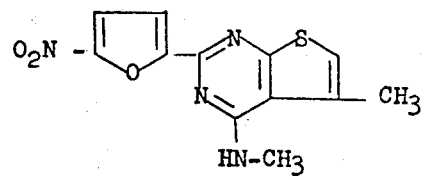

was prepared from 4-chloro-5-methyl-2-(5′-nitro-2′-furyl)-thieno[2,3-d]pyrimidine and methylamine.

EXAMPLE 24

Using a procedure analogous to that described in Example 1, 4-(β-hydroxyethyl-amino)-5-methyl-2-(5′-nitro-2′-furyl)-thieno[2,3-d]pyrimidine, m. p. 211°–212°C. (recrystallized from methyl ethyl ketone), was prepared from 4-chloro-5-methyl-2-(5′-nitro-2′-furyl)-thieno[2,3-d]pyrimidine and 2-amino-ethanol.

EXAMPLE 25

Using a procedure analogus to that described in Example 1, 4-(β-hydroxyethyl-amino)-6-methyl-2-(5′-nitro-2′-furyl)-thieno[2,3-d]pyrimidine, m. p. 170°C. (recrystallized from ethanol), of the formula

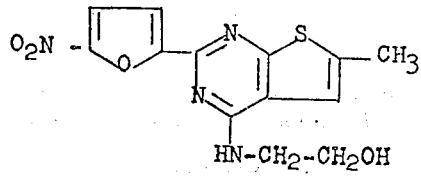

was prepared from 4-chloro-6-methyl-2-(5′-nitro-2′-furyl)-thieno[2,3-d]pyrimidine and 2-amino-ethanol.

EXAMPLE 26

Using a procedure analogous to that described in Example 1, 4-(β-hydroxypropyl-amino)-6-methyl-2-(5′-nitro-2′-furyl)-thieno[2,3-d]pyrimidine, m. p. 215°–216°C. (recrystallized from methyl ethyl ketone), was prepared from 4-chloro-6-methyl-2-(5′-nitro-2′-furyl)-thieno[2,3-d]pyrimidine and 1-amino-propanol-2.

EXAMPLE 27

Using a procedure analogous to that described in Example 1, 4-methylamino-6-ethyl-2-(5′-nitro-2′-furyl)-thieno[2,3-d]pyrimidine, m. p. 179°–180°C. (recrystallized from ethanol), was prepared from 4-chloro-6-ethyl-2-(5′-nitro-2′-furyl)-thieno[2,3-d]pyrimidine and methylamine.

EXAMPLE 28

Using a procedure analogous to that described in Example 1, 4-(β-hydroxyethyl-amino)-6-ethyl-2-(5'-nitro-2'-furyl)-thieno[2,3-d]pyrimidine, m. p. 194°–195°C. (recrystallized from ethanol), was prepared from 4-chloro-6-ethyl-2-(5'-nitro-2'-furyl)-thieno[2,3-d]pyrimidine and 2-amino-ethanol.

EXAMPLE 29

Using a procedure analogous to that described in Example 1, 4-(β-hydroxyethyl-amino)-5,6-dimethyl-2-(5'-nitro-2'-furyl)-thieno[2,3-d]pyrimidine, m. p. 201°–202°C. (recrystallized from dioxane), of the formula

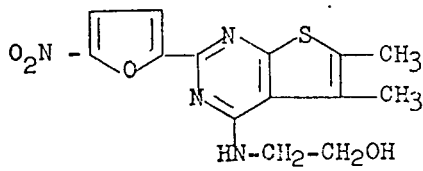

was prepared from 4-chloro-5,6-dimethyl-2-(5'-nitro-2'-furyl)-thieno[2,3-d]pyrimidine and 2-amino-ethanol.

EXAMPLE 30

4-[(β-acetylamino-ethyl)-amino]2-(5'-nitro-2'-furyl)-thieno[2,3-d]pyrimidine by method A A solution of 1.0 gm (0.01 mol) of N-acetyl-ethylenediamine in 5 ml of dimethylsulfoxide was added dropwise to a suspension of 1.4 gm (0.005 mol) of 4-chloro-2-(5'-nitro-2'-furyl)-thieno[2,3-d]pyrimidine in 20 ml of dimethylsulfoxide at 70°C., accompanied by stirring, and the resulting mixture was maintained at that temperature for one hour, whereby a solution was formed. Thereafter, the solution was cooled and then poured into water, and the precipitate formed thereby was collected by vacuum filtration, washed with water and recrystallized from ethanol, yielding 0.97 gm (56% of theory) of the compound of the formula

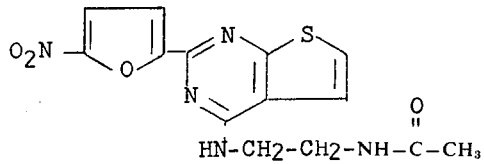

having a melting point of 257°C.

Analysis: $C_{14}H_{13}N_5O_4S$; mol. wt. 347.36: Calculated (percent): C, 48.41; H, 3.78; N, 20.16 Found (percent): C, 48.50; H, 3.90; N, 20.27

EXAMPLE 31

Using a procedure analogous to that described in Example 30, 4-[(β-acetylamino-ethyl)-amino]-5-methyl-2-(5'-nitro-2'-furyl)-thieno[2,3-d]pyrimidine, m. p. 235°–236°C. (from dimethylformamide), was prepared from 4-chloro-5-methyl-2-(5'-nitro-2'-furyl)-thieno[2,3-d]pyrimidine and N-acetyl-ethylenediamine.

EXAMPLE 32

Using a procedure analogous to that described in Example 30, 4-[β-acetylamino-ethyl)-amino]-6-methyl-2-(5'-nitro-2'-furyl)-thieno[2,3-d]pyrimidine, m. p. 257°–258°C. (from dimethylformamide), was prepared from 4-chloro-6-methyl-2-(5'-nitro-2'-furyl)-thieno[2,3-d]pyrimidine and N-acetyl-ethylenediamine.

EXAMPLE 33

Using a procedure analogous to that described in Example 30, 4-[(β-acetylamino-ethyl)-amino]-5,6-dimethyl-2-(5'-nitro-2'-furyl)-thieno[2,3-d]pyrimidine, m. p. 256°–258°C. (from dimethylformamide), was prepared from 4-chloro-5,6-dimethyl-2-(5'-nitro-2'-furyl)-thieno[2,3-d]pyrimidine and N-acetyl-ethylenediamine.

EXAMPLE 34

4-(β-Aminoethyl-amino)-2-(5'-nitro-2'-furyl)-thieno[2,3-d]pyrimidine hydrochloride by method A A mixture consisting of 3.5 gm (0.01 mol) of 4-[β-acetylamino-ethyl)-amino]-2-(5'-nitro-2'-furyl)-thieno[2,3-d]pyrimidine and 25 ml of concentrated hydrochloric acid was heated for ten hours on a boiling water bath. Thereafter, the resulting reaction solution was evaporated to dryness, and the residue was recrystallized from aqueous ethanol, yielding 1.8 gm of the compound of the formula

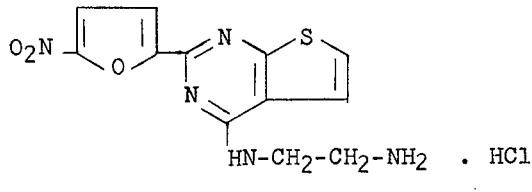

having a melting point of 283°–285°C.

Analysis: $C_{12}H_{11}N_5O_3S \cdot HCl$; mol. wt. 341.79: Calculated (percent): C, 42.16; H, 3.54; Cl, 10.38 Found (percent): C, 42.20; H, 3.56; Cl, 10.24

EXAMPLE 35

Using a procedure analogous to that described in Example 34, 4-(β-aminoethyl-amino)-5-methyl-2-(5'-nitro-2'-furyl)-thieno[2,3-d]pyrimidine hydrochloride, m. p. >290°C. (from aqueous ethanol), was prepared from 4-[(β-acetylamino-ethyl)-amino]-5-methyl-2-(5'-nitro-2'-furyl)-thieno[2,3-d]pyrimidine and concentrated hydrochloric acid.

EXAMPLE 36

Using a procedure analogous to that described in Example 34, 4-(β-aminoethyl-amino)-6-methyl-2-(5'-nitro-2'-furyl)-thieno[2,3-d]pyrimidine hydrochloride, m. p. 300°–302°C. (from aqueous ethanol), was prepared from 4-[(β-acetylamino-ethyl)-amino]-6-methyl-2-(5'-nitro-2'-furyl)-thieno[2,3-d]pyrimidine and concentrated hydrochloric acid.

EXAMPLE 37

Using a procedure analogous to that described in Example 34, 4-(β-aminoethyl-amino)-5,6-dimethyl-2-(5'-nitro-2'-furyl)-thieno[2,3-d]pyrimidine hydrochloride, m. p. >300°C. (from aqueous ethanol), was prepared from 4-[(β-acetylamino-ethyl)-amino]-5,6-dimethyl-2-(5'-nitro-2'-furyl)-thieno[2,3-d]pyrimidine and concentrated hydrochloric acid.

EXAMPLE 38

4-Dibutylamino-2-(5'-nitro-2'-furyl)-thieno[2,3-d]pyrimidine by method A

A mixture consisting of 1.45 gm (0.005 mol) of 4-methylmercapto-2-(5'-nitro-2'-furyl)-thieno[2,3-d]pyrimidine and 20 ml of dibutylamine was refluxed for 3 hours. Thereafter, the excess, unreacted dibutylamine was distilled off in vacuo, and the residue was purified by column chromatography on silicagel (particle size 0.2 – 0.5 mm), using a mixture of benzene and acetone (9:1) as the flow agent. 0.4 gm (21% of theory) of the compound of the formula

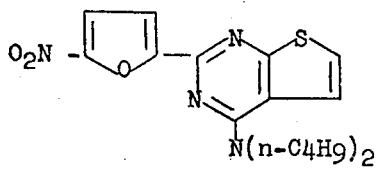

having a melting point of 102°–103°C. was obtained.

Analysis: $C_{18}H_{22}N_4O_3S$; mol. wt. 374.47: Calculated (percent): C, 57.73; H, 5.92; N, 14.06 Found (percent): C, 57.70; H, 6.00; N, 15.00

EXAMPLE 39

4-[(β-Acetoxy-ethyl)-amino]-2-(5'-nitro-2'-furyl)-thieno[2,3-d]pyrimidine by method B 0.2 ml of concentrated nitric acid was added to a solution of 3.0 gm (0.01 mol) of 4-[(β-acetoxy-ethyl)-amino]-2-(2'-furyl)-thieno[2,3-d]pyrimidine (m. p. 143°–145°C., recrystallized from ethyl acetate/hexane) in 30 ml of acetic acid anhydride at room temperature, the mixture was cooled to −15°C., and then 10 ml of concentrated sulfuric acid were added dropwise. The reaction mixture was allowed to stand for 15 minutes and was then poured over ice. The resulting aqueous mixture was neutralized (pH 6) with concentrated ammonia while cooling, and the precipitate formed thereby was collected by vacuum filtration and purified by column chromatography on silicagel (particle size 0.2 – 0.5 mm), using a mixture of benzene and acetone (8:2) as the flow agent. 0.73 gm (21% of theory) of the compound of the formula

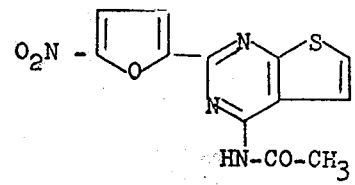

having a melting point of 182°–183°C. was obtained.

Analysis: $C_{14}H_{12}N_4O_5$; mol. wt. 348.34: Calculated (percent): C, 48.28; H, 3.48; N, 16.09. Found (percent): C, 48.40; H, 3.55; N, 15.98.

EXAMPLE 40

Using a procedure analogous to that described in Example 39, 4-(β-acetoxy-propyl)-amino]-2-(5'-nitro-2'-furyl)-thieno[2,3-d]pyrimidine, m. p. 148°–150°C., of the formula

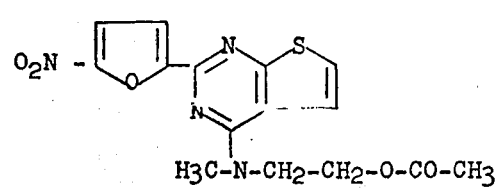

was prepared from 4-[(β-acetoxy-propyl)-amino]-2-(2'-furyl)-thieno[2,3-d]pyrimidine and nitric acid.

EXAMPLE 41

Using a procedure analogous to that described in Example 39, 4-[N-(β-acetoxy-ethyl)-methylamino]-2-(5'-nitro-2'-furyl)-thieno[2,3-d]pyrimidine, m. p. 134°–135°C., of the formula was prepared from 4-[N-(β-acetoxy-ethyl)-methylamino]-2-(2'-furyl)-thieno[2,3-d]pyrimidine and nitric acid.

EXAMPLE 42

Using a procedure analogous to that described in Example 39, 4-acetamino-2-(5'-nitro-2'-furyl)-thieno[2,3-d]pyrimidine, m. p. 278°–280°C., of the formula was prepared from 4-acetamino-2-(2'-furyl)-thieno[2,3-d]pyrimidine and nitric acid.

EXAMPLE 43

2-(5'-Nitro-2'-furyl)-4-propionylamino-thieno[2,3-d]pyrimidine by method E

A suspension of 2.6 gm (0.01 mol) of 4-amino-2-(5'-nitro-2'-furyl)-thieno[2,3-d]pyrimidine in 20 ml of propionyl chloride was refluxed for 3-½ hours, accompanied by vigorous stirring. Thereafter, the reaction mixture was cooled, and the solid component was collected by vacuum filtration, washed with methylene chloride and with water, dried and recrystallized from tetrahydrofuran, yielding 1.9 gm (60% of theory) of the compound of the formula

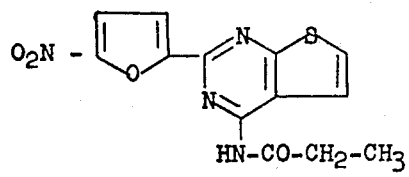

having a melting point of 215°–217°C.

Analysis: $C_{13}H_{10}N_4O_4S$; mol. wt. 318.32: Calculated (percent): C, 49.05; H, 3.18; N, 17.60 Found (percent): C, 49.21; H, 3.27; N, 17.44

EXAMPLE 44

Using a procedure analogous to that described in Example 43, 4-chloroacetamino-2-(5'-nitro-2'-furyl)-thieno[2,3-d]pyrimidine, m. p. 263°C. (from methyl ethyl ketone), of the formula

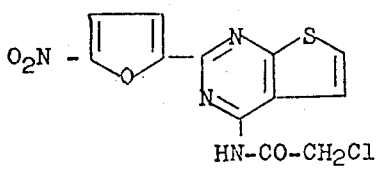

HN–CO–CH$_2$Cl was prepared from 4-amino-2-(5'-nitro-2'-furyl)-thieno[2,3-d]pyrimidine and chloroacetyl chloride.

EXAMPLE 45

Using a procedure analogous to that described in Example 43, 4-dichloroacetamino-2-(5'-nitro-2'-furyl)-thieno[2,3-d]pyrimidine, m. p. 245°–246°C. (from methyl ethyl ketone), of the formula

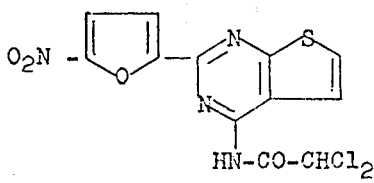

HN–CO–CHCl$_2$ was prepared from 4-amino-2-(5'-nitro-2'-furyl)-thieno[2,3-d]pyrimidine and dichloroacetyl chloride.

The compounds embraced by formula I above and their non-toxic, pharmacologically acceptable acid addition salts, have useful pharmacodynamic properties. More particularly, they exhibit bactericidal, fungicidal and trichomonacidal activities. As bactericides they are effective against grampositive as well as gram-negative bacteria, and as trichomonacides they are especially effective against trichomonas vaginalis.

The antibacterial activity was ascertained by the agar-diffusion test and by the series dilution test in close analogy to the test method described by P. Klein in "Bakteriologische Grundlagen der Chemotherapeutischen Laboratoriumspraxis," Springer-Verlag, Stuttgart, Germany (1957), pages 53–76 and 87–109.

The following compounds, for example, were found to be particularly good antibacterial agents against Staphylococcus aureus SG 511 and Streptococcus Aronson even at concentrations of as low as less than 5 γ/ml, and against E. Coli even at concentrations as low as less than 25 γ/ml:

4-Methylamino-2-(5'-nitro-2'-furyl)-thieno[2,3-d]pyrimidine,

4-Ethylamino-2-(5'-nitro-2'-furyl)-thieno[2,3-d]pyrimidine,

4-Isopropylamino-2-(5'-nitro-2'-furyl)-thieno[2,3-d]pyrimidine, 4-(β-Hydroxyethyl-amino)-2-(5'-nitro-2'-furyl)-thieno[2,3-d]pyrimidine, 4-(β,γ-Dihydroxypropyl-amino)-2-(5'-nitro-2'-furyl)-thieno[2,3-d]pyrimidine, 4-(β-Methoxyethyl-amino)-2-(5'-nitro-2'-furyl)-thieno[2,3-d]pyrimidine, and 4-(β-Aminoethyl-amino)-2-(5'-nitro-2'-furyl)-thieno[2,3-d]pyrimidine.

The following compounds exhibit particularly powerful trichomonacidal action against Trichomonas vaginalis, even at concentrations of as low as less than 0.1 γ/ml:

4-(β-Hydroxyethyl-amino)-2-(5'-nitro-2'-furyl)-thieno[2,3-d]pyrimidine, 4-(Bis[β-hydroxyethyl]-amino)-2-(5'-nitro-2'-furyl)-thieno [2,3-d]pyrimidine, 4-(N-[β-Hydroxyethyl]-methylamino)-2-(5'-nitro-2'-furyl)-thieno[2,3-d]pyrimidine, 4-(Bis-[β-Hydroxypropyl]-amino)-2-(5'-nitro-2'-furyl)-thieno[2,3-d]pyrimidine, and 4-(β-Methoxyethyl-amino)-2-(5'-nitro-2'-furyl)-thieno[2,3-d]pyrimidine.

For pharmaceutical purposes the compounds of the formula I or their non-toxic acid addition salts are administered to warm-blooded animals topically or per-orally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral dosage unit of the compounds according to the present invention is from 0.166 to 3.33 mgm/kg body weight, preferably 0.83 to 1.67 mgm/kg body weight.

The following examples illustrate a few pharmaceutical compositions comprising a compound of the present invention as an active ingredient and represent the best modes contemplated of putting the invention into practical use. The parts are parts by weight unless otherwise specified.

EXAMPLE 46

Tablets

The tablet composition is compounded from the following ingredients:

| | | |
|---|---:|---|
| 4-Methylamino-2-(5'-nitro-2'-furyl)-thieno[2,3-d]pyrimidine | 100.0 | parts |
| Lactose | 63.0 | " |
| Potato starch | 50.0 | " |
| Polyvinylpyrrolidone | 5.0 | " |
| Magnesium stearate | 2.0 | " |
| Total | 220.0 | parts |

Preparation:

The thienopyrimidine compound is intimately admixed with the lactose and the potato starch, the mixture is moistened with an aqueous 10% solution of the polyvinylpyrrolidone, the moist mass is forced through a 1.5 mm-mesh screen, and the resulting granulate is dried at 45°C. and again passed through the screen. The dry granulate is admixed with the magnesium stearate, and the composition is compressed into 220 mgm-tablets in a conventional tablet making machine. Each tablet contains 100 mgm of the thienopyrimidine compound and is an oral dosage unit composition with effective antibacterial action.

EXAMPLE 47

Coated Pills

The pill core composition is compounded from the following ingredients:

| | | |
|---|---|---|
| 4-Methylamino-2-(%'-nitro-2'-furyl)-thieno[2,3-d]pyrimidine | 50.0 | parts |
| Lactose | 30.0 | " |
| Corn starch | 30.0 | " |
| Gelatin | 3.0 | " |
| Cellulose, microcrystalline | 6.0 | " |
| Magnesium stearate | 1.0 | " |
| Total | 120.0 | parts |

Preparation:

The thienopyrimidine compound is intimately admixed with the lactose and the corn starch, the mixture is moistened with an aqueous 12% solution of the gelatin, the moist mass is forced through a 1.5 mm-mesh screen, and the resulting granulate is dried at 45°C. and again passed through a 1.0 mm-mesh screen. The dry granulate is admixed with the cellulose and the magnesium stearate, and the composition is compressed into 120 mgm-pill cores, which are subsequently coated in conventional manner with a thin shell consisting essentially of a mixture of talcum and sugar and finally polished with beeswax. Each coated pill contains 50 mgm of the thienopyrimidine compound and is an oral dosage unit composition with effective antibacterial action.

EXAMPLE 48

Vaginal Tablets

The tablet composition is compounded from the following ingredients:

| | | |
|---|---|---|
| 4-(β-Methoxyethyl-amino)-2-(5'-nitro-2'-furyl)-thieno[2,3-d]pyrimidine | 100.0 | parts |
| Sorbitol | 885.0 | " |
| Carboxymethyl cellulose, high viscosity | 10.0 | " |
| Magnesium stearate | 5.0 | " |
| Total | 1000.0 | parts |

Preparation:

The thienopyrimidine compound is intimately admixed with the sorbitol and the carboxymethyl cellulose, the mixture is moistened with aqueous 50% ethanol (150 gm per 1000 tablets), the moist mass is forced through a 2 mm-mesh screen, the resulting granulate is dried at 45°C. and again passed through the screen, the dry granulate is admixed with the magnesium stearate, and the composition is compressed in conventional manner into 1000 mgm-vaginal tablets. Each tablet contains 100 mgm of the thienopyrimidine compound and is a dosage unit composition with effective trichomonacidal action against *Trichomonas vaginalis*.

EXAMPLE 49

Tincture

The tincture is compounded from the following ingredients:

| | | |
|---|---|---|
| 4-(β-Aminoethyl-amino)-2-(5'-nitro-2'-furyl)-thieno[2,3-d]pyrimidine | 1.0 | parts |
| Polyethyleneglycol 400 | 99.0 | " |
| Total | 100.0 | parts |

Preparation:

The thienopyrimidine compound is dissolved in the polyethyleneglycol by warming, and the solution is cooled and filtered. The filtrate contains 1% by weight of the thienopyrimidine compound and is a topical composition with effective antibacterial action.

EXAMPLE 50

Lotion

The lotion is compounded from the following ingredients:

| | | |
|---|---|---|
| 4-Ethylamino-2-(5'-nitro-2'-furyl-thieno[2,3-d]pyrimidine | 1.0 | parts |
| Sorbitan monopalmitate (Span 40) | 1.0 | " |
| Long-chain, high-molecular-weight polyglycolether, water-soluble (Cremophor O) | 2.0 | " |
| Cetyl stearyl alcohol (Lanette O) | 2.0 | " |
| Spermaceti | 1.0 | " |
| Decyl oleate | 5.0 | " |
| Paraffin oil | 1.0 | " |
| Distilled water | 87.0 | " |
| Total | 100.0 | parts |

Preparation:

The inert ingredients of the dispersed phase are admixed, and the mixture is melted, heated to 70°C. and then emulsified into the distilled water at the same temperature. The aqueous emulsion is cooled to 40°C., the finely milled thienopyrimidine compound is suspended therein with the aid of an immersion homogenizer, and the suspension is cooled to room temperature. The resulting lotion contains 1% by weight of the thienopyrimidine compound and is a topical composition with effective antibacterial action.

EXAMPLE 51

Coated pills with combination of active ingredients

The pill core composition is compounded from the following ingredients:

| | | |
|---|---|---|
| 4-(β-Hydroxyethyl-amino)-2-(5'-nitro-2'-furyl)-thieno[2,3-d]pyrimidine | 50.0 | parts |
| Papaverine | 25.0 | " |
| Corn starch | 32.0 | " |
| Gelatin | 3.0 | " |
| Cellulose, microcrystalline | 9.0 | " |
| Magnesium stearate | 1.0 | " |
| Total | 120.0 | parts |

The pills are compounded and manufactured in the same way as in Example 47. Each coated pill contains 50 mgm of the thienopyrimidine compound and 25 mgm of papaverine and is an oral dosage unit composition with effective antibacterial and smooth muscle relaxing actions.

EXAMPLE 52

Gelatin Capsules

The capsule filler composition is compounded from the following ingredients:

| | | |
|---|---|---|
| 4-[Bis-(β-hydroxy-ethyl)-amino]-2-(5'-nitro-2'furyl)-thieno[2,3-d]pyrimidine | 150.0 | parts |
| Lactose | 100.0 | " |
| Talcum | 50.0 | " |
| Total | 300.0 | parts |

Preparation:

The ingredients are intimately admixed with each other, the mixture is passed through a 1.0 mm-mesh screen, and 300 mgm-portions of the resulting composition are filled into gelatin capsules of suitable size. Each capsule contains 150 mgm of the thienopyrimidine compound and is an oral dosage unit composition with effective antibacterial and trichomonacidal action.

Analogous results are obtained when any one of the other thienopyrimidines embraced by formula I or a nontoxic acid addition salt thereof is substituted for the particular thienopyrimidine in Examples 46 through 52. Likewise, the amount of active ingredient in these illustrative examples may be varied to achieve the dosage unit range or concentration set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A biocidal pharmaceutical dosage unit composition consisting essentially of an inert pharmaceutical carrier and an effective bactericidal, fungicidal or trichomonacidal amount of a compound of the formula

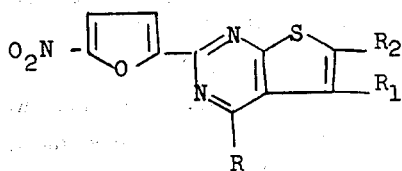

wherein
R is amino; (alkanoyl of 2 to 3 carbon atoms)amino; chloroacetyl-amino; dichloroacetyl-amino; mono-(alkyl of 1 to 5 carbon atoms)-amino; di(alkyl of 1 to 4 carbon atoms)-amino; mono(hydroxyalkyl of 1 to 5 carbon atoms)-amino; di(hydroxyalkyl of 2 to 3 carbon atoms)-amino; N-(alkyl of 1 to 4 carbon atoms)-hydroxyethylamino; dihydroxypropyl-amino; (alkoxy of 1 to 2 carbon atoms)-(alkylene of 2 to 3 carbon atoms)-amino; aminoethyl-amino; acetaminoethyl-amino; acetoxy-(alkylene of 2 to 3 carbon atoms)-amino; N-acetoxyethyl-methylamino; or hydroxy-piperidino; and $R_1$ and $R_2$ are each hydrogen, methyl or ethyl, or a non-toxic, pharmacologically acceptable acid addition salt thereof.

2. The composition of claim 1, where said compound is 4-methylamino-2-(5'-nitro-2'-furyl)-thieno[2,3-d]pyrimidine or a non-toxic, pharmacologically acceptable acid addition salt thereof.

3. The composition of claim 1, where said compound is 4-ethylamino-2-(5'-nitro-2'-furyl)-thieno[2,3-d]pyrimidine or a non-toxic, pharmacologically acceptable acid addition salt thereof.

4. The composition of claim 1, where said compound is 4-isopropylamino-2-(5'-nitro-2'-furyl)-thieno[2,3-d]pyrimidine or a non-toxic, pharmacologically acceptable acid addition salt thereof.

5. The composition of claim 1, where said compound is 4-(β-hydroxyethyl-amino)-2-(5'-nitro-2'-furyl)-thieno[2,3-d]pyrimidine or a non-toxic, pharmacologically acceptable acid addition salt thereof.

6. The composition of claim 1, where said compound is 4-(β,γ-dihydroxypropyl-amino)-2-(5'-nitro-2'-furyl)-thieno[2,3-d]pyrimidine or a non-toxic, pharmacologically acceptable acid addition salt thereof.

7. The composition of claim 1, where said compound is 4-(β-methoxyethyl-amino)-2-(5'-nitro-2'-furyl)-thieno[2,3-d]pyrimidine or a non-toxic, pharmacologically acceptable acid addition salt thereof.

8. The composition of claim 1, where said compound is 4-(β-aminoethyl-amino)-2-(5'-nitro-2'-furyl)-thieno[2,3-d]pyrimidine or a non-toxic, pharmacologically acceptable acid addition salt thereof.

9. The composition of claim 1, where said compound is 4-[bis-(β-hydroxyethyl)-amino]-2-(5'-nitro-2'-furyl)-thieno[2,3-d]pyrimidine or a non-toxic, pharmacologically acceptable acid addition salt thereof.

10. The composition of claim 1, where said compound is 4-[N-(β-hydroxyethyl)-methyl-amino]-2-(5'-nitro-2'-furyl)-thieno[2,3-d]pyrimidine or a non-toxic, pharmacologically acceptable acid addition salt thereof.

11. The composition of claim 1, where said compound is 4-[bis-(β-hydroxypropyl)-amino]-2-(5'-nitro-2'-furyl)-thieno[2,3-d]pyrimidine or a non-toxic, pharmacologically acceptable acid addition salt thereof.

12. A method of killing microorganisms selected from the group consisting of bacteria, fungi and trichomonads, which comprises contacting said microorganisms with an effective bactericidal, fungicidal or trichomonacidal amount of a compound of the formula

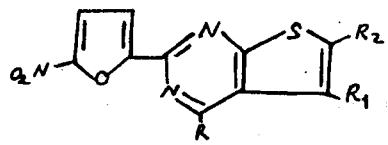

wherein
R is amino; (alkanoyl of 2 to 3 carbon atoms)-amino; chloroacetyl-amino; dichloroacetyl-amino; mono-(alkyl of 1 to 5 carbon atoms)-amino; di(alkyl of 1 to 4 carbon atoms)-amino; mono(hydroxyalkyl of 1 to 5 carbon atoms)-amino; di(hydroxyalkyl of 2 to 3 carbon atoms)-amino; N-(alkyl of 1 to 4 carbon atoms)-hydroxyethylamino; dihydroxypropyl-amino; (alkoxy of 1 to 2 carbon atoms)-(alkylene of 2 to 3 carbon atoms)-amino; aminoethyl-amino; acetaminoethyl-amino; acetoxy(alkylene of 2 to 3 carbon atoms)-amino; N-acetoxy-ethyl-methylamino; or hydroxy-piperidino; and $R_1$ and $R_2$ are each hydrogen, methyl or ethyl, or a non-toxic, pharmacologically acceptable acid addition salt thereof.

* * * * *

UNITED STATES PATENT OFFICE
CERTIFICATE OF CORRECTION

Patent No. 3,932,642  Dated January 13, 1976

Inventor(s) EBERHARD WOITUN and WOLFGANG REUTER

It is certified that error appears in the above-identified patent and that said Letters Patent are hereby corrected as shown below:

In Col. 5, Line 54    "ether" should read -- ethyl --

In Col. 8, Line 67    "1.29" should read -- 16.29 --

In Col. 21, Example 47    Compound "4-Methylamino-2-(%'" should read -- 4-Methylamino-2-(5' --

Signed and Sealed this sixth Day of April 1976

[SEAL]

Attest:

RUTH C. MASON
Attesting Officer

C. MARSHALL DANN
Commissioner of Patents and Trademarks